United States Patent
Gray et al.

(10) Patent No.: US 6,526,120 B1
(45) Date of Patent: *Feb. 25, 2003

(54) X-RAY FLOW RATE MEASUREMENT SYSTEM FOR MATERIALS, INCLUDING AGRICULTURAL MATERIALS AND FOOD PRODUCTS

(76) Inventors: Joseph N. Gray, 5614 Valley Rd., Ames, IA (US) 50010; Feyzi Inanc, 2035 Wyngate Dr., Ames, IA (US) 50010; Selcuk Arslan, 136-C University Village, Ames, IA (US) 50011

(*) Notice: Subject to any disclaimer, the term of this patent is extended or adjusted under 35 U.S.C. 154(b) by 0 days.

This patent is subject to a terminal disclaimer.

(21) Appl. No.: 09/304,899

(22) Filed: May 4, 1999

Related U.S. Application Data
(60) Provisional application No. 60/084,421, filed on May 6, 1998.

(51) Int. Cl.[7] .............................................. G01N 23/04
(52) U.S. Cl. .......................... 378/57; 378/51; 56/10.2 R
(58) Field of Search .................. 378/51, 57; 56/10.2 R, 56/10.1, 10.2 J

(56) References Cited

U.S. PATENT DOCUMENTS

| | | | |
|---|---|---|---|
| 4,055,989 A | * 11/1977 | Henry, Jr. et al. | ............. 73/637 |
| 4,413,280 A | * 11/1983 | Adlerstein et al. | .......... 358/111 |
| 4,686,085 A | 8/1987 | Osterholm | |
| 4,765,190 A | 8/1988 | Strubbe | |
| 4,830,849 A | * 5/1989 | Osterholm | |
| 4,961,304 A | 10/1990 | Ovsborn | |
| 5,065,632 A | 11/1991 | Reuter | |
| 5,218,346 A | * 6/1993 | Meixler | |
| 5,487,702 A | 1/1996 | Campbell | |
| 5,561,250 A | 10/1996 | Myers | |
| 5,563,929 A | * 10/1996 | Connolly et al. | ............. 378/51 |
| 5,686,671 A | 11/1997 | Nelson | |
| 5,774,357 A | * 6/1998 | Hoffberg et al. | ............ 364/188 |

OTHER PUBLICATIONS

B. Missotten, G. Strubbe, J. De Baerdemaeker; Accuracy of Grain and Straw Yield Mapping; Dtd. —Unknown; pp. 713–722; Madison, Wisconsin; *Precision Agriculture*, Copyright 1996.

R. Vansichen, J. DeBaerdemaeker; Continuous Wheat Yield Measurement On a a Combine, Automated Agriculture for the 21st Century, Proceedings of the 1991 Symposium, St. Joseph ASAE Publication; Nov. 1991.

T. S. Colvin, D. L. Karlen, J.R. Ambuel, F. Perez–Munoz; Yield Monitoring For Mapping; 1995; *Site–Specific Management for Agricultural Systems*,Published by ASAE; pp. 3–14; Madison, Wisconsin.

J.V. Stafford, B. Ambler, M.P. Smith; Sensing and Mapping Grain Yield Variation; Automated Agriculture for the 21st Century, Proceedings of the 1991 Symposium, St. Joseph ASAE Publication; Nov. 1991; pp. 356–366.

(List continued on next page.)

Primary Examiner—David V. Bruce
Assistant Examiner—Pamela R. Hobden

(57) ABSTRACT

The present invention is an apparatus and method for measuring flow rate of materials, for example the flow rate of agricultural products. The apparatus includes an x-ray generator positioned near flowing materials, a converter for converting the x-ray radiation which passes through the flowing materials into visible light, a camera for capturing images of the visible light, and a processor for processing the images to determine the flow rate. The invention may also include an image intensifier to intensify the images before being converted by the camera. The method directs x-rays through flowing material, converts the x-rays to visible light, records the intensity of the visible light and derives the flow rate from the intensity measures.

36 Claims, 4 Drawing Sheets

OTHER PUBLICATIONS

Abstract—Myers; U.S. Pat. 5,343,761; Issue Date: Sep. 6, 1994.

Stuart J. Birrell, Kenneth A. Sudduth, Steven C. Borgelt; Comparison of Sensors and Techniques for Crop Yield Mapping; Dtd. Sep. 29, 1995; pp. 215–233; *Elsevier Science B.V.* .

B. Missotten, G. Strubbe, J. De Baerdemaeker; Accuracy of Grain and Straw Yield Mapping; Dtd.—Unknown; pp. 713–722; Madison, Wisconsin; *Precision Agriculture*.

F. Perez–Munoz, T. S. Colvin; Continuous Grain Yield Monitoring; 1996; *Transactions of the ASAE*, pp. 1–9.

Barry L. Stott, Steven C. Borgelt, Kenneth A. Sudduth; Yield Determination Using An Instrumented Claas Combine; ASAE Mtg. Dates Dec. 14/17, 1993; Presentation Paper #931507; pp. 1–24; St. Joseph, MI.

H. Auernhammer, M. Demmel, K. Muhr, J. Rottmeier, K. Wild; Yield Measurements on Combine Harvesters; ASAE Mtg. Dates Dec 12–17, 1993; Presentation Paper #931506; pp. 1–8; St. Joseph, Michigan.

R. Vansichen, J. De Baedemaeker; Continuous Wheat Yield Measurement On a Combine; pp. 346–355.

T. S. Colvin, D. L. Karlen, J.R. Ambuel, F. Perez–Munoz; Yield Monitoring For Mapping For Mapping; 1995; *Site–Specific Management for Agricultural Systems*, pp. 3–14; Madison, Wisconsin.

J.V. Stafford, B. Ambler, M.P. Smith; Sensing and Mapping Grain Yield Variation; pp. 356–366.

S.N. Pang, G.C. Zoerb, A Grain Flow Sensor For Yield Mapping; ASAE Mtg. Dates Dec. 18–21, 1990; Presentation Paper #901633, pp. 1–10; St. Joseph, Michigan.

J.L. Pringle, M.D. Schrock, R.T. Hinnen, K.D. Howard, D.L. Oard; Yield Variation in Grain Crops; ASAE Mtg. Dates Dec. 14–17, 1993; Presentation Paper #931505, pp. 1–10; St. Joseph, Michigan.

G.J. Strubbe, B. Missotten, J. De Baerdemaeker, Mass Flow Measurement with a Curved Plate at the Exit of an Elevator; 1996; pp. 703–711; Madison, Wisconsin.

* cited by examiner

X-RAY FLOW RATE MEASUREMENT SYSTEM FOR MATERIALS, INCLUDING AGRICULTURAL MATERIALS AND FOOD PRODUCTS

This application claims the benefit of U.S. Provisional Application Ser. No. 60/084,421 May 6, 1998.

BACKGROUND OF THE INVENTION

Field of the Invention

The present invention relates to mass flow monitoring of materials, including agricultural materials and food products. More particularly, though not exclusively, the present invention relates to a method and apparatus for using x-ray techniques for monitoring flow rate of materials including biological materials.

Flow rate measurement of agricultural materials and food products is a subject that appears frequently during harvesting, handling and transportation, and in food processing, conveying, and storage stages. While measuring the amount of crop being loaded to/from various transportation vehicles is important for obvious reasons, knowing the amount of material flowing into various physical or chemical processes at food processing plants is vitally important for a proper blend of various elements to go into these processes. In addition to these, in farming, crop flow rate measurement is a subject to growing interest at the harvest stage as well. This forms an important element of a new concept known as precision farming briefly described below.

There is considerable spatial variability in soil properties such as nutrient availability and pH levels within a given field. Factors such as water availability, poor drainage, and variations in topography introduce other dimensions to spatial variabilities resulting in varying yield patterns within a single field. These variabilities traditionally have not been taken into account when practicing soil and crop management. Applying uniform input rates of fertilizers and chemicals may result in excessive agrochemical deposition in some of the areas of a field depending on local requirements. Conventional farm management thus contains two major drawbacks. First, higher application rates than necessary in a certain location would increase the application cost. Second, excessive input application causes surface and groundwater contamination through surface runoff and chemical leaching.

Therefore, it makes more sense to vary application rates of agricultural inputs depending upon the localized needs in a field. This management strategy would help optimize yield obtained from locations having different fertility levels. Thus, as opposed to field-based practices, variable rates of physical and chemical inputs (such as seeds, water, fertilizers and chemicals, and tilling of the soil) should be applied to different areas of a field. In order to achieve this goal, regions of a field with the same yield potential need to be mapped. Creating management zones (small management areas) would help identify the cause-and-effects of the local yield variability. Geographic Information Systems (GIS) can be used to store the spatial soil and yield data, analyze and display results in the form of tables and/or maps, and identify most promising crop and management practices.

The adoption of precision farming includes two major thrusts. One involves the evaluation of outcomes of certain physical and chemical procedures implemented in the field on the basis of databases formed through data acquisition over years. The data acquisition includes yield data in order to generate crop yield maps. Agricultural crop flow measurement is a key parameter in forming yield maps, and accurate measurement of flow rate has a lasting impact on forming reliable databases to be used in precision farming. The second thrust involves development of new machinery, equipment, and sensors to be used in precision farming practices. Specifically, the development of more advanced sensors for data acquisition is very important and will have a lasting impact on overall precision farming activities.

To practice site-specific farming (also known as prescription farming, precision farming, site-specific management, spatially variable farm management, and variable rate technology (VRT)), the position of farm equipment must be determined accurately in real-time while working in the field. By knowing the precise location of the farm equipment, inputs can be applied using predetermined application rates. Amongst various position determination methods, Differential Global Positioning System (DGPS) is the most effective means of 3-D positioning. The location data can be tagged with spatial data to generate maps of applications rates, yield, moisture, pH, and other variables of interest.

The cause-and-effects of yield need to be determined to be able to optimize yield spatially and to reduce environmental contamination due to chemical applications. This requires accurate mass flow rate measurement for materials being harvested since yield maps provide understanding about crop response to various crop management practices in a specified management zone.

METHODS OF FLOW RATE MEASUREMENTS

Many methods have been used in an attempt to measure flow rates of agricultural products. Two types of yield monitors have been used in the prior art: mass flow meters and volumetric flow meters. Mass flow meters determine the mass of flowing material continuously. Volumetric flow meters are used to measure the volume of product on-the-go as well. The measured volume is converted into standard mass by the manipulation of appropriate conversions.

Commercial volume-based sensors include a paddle-wheel sensor and an infrared sensor (photo-optical sensor). Research prototypes of volumetric sensors include an ultrasonic sensor and Light Emitting Diodes (LED). Commercial mass flow rate sensors available to farmers are impact-based plate sensors (strain-gage based load cells, weigh pads, and potentiometers), a nuclear sensor (gamma ray sensor), and conveyor belts. Examples of research prototypes of mass flow sensors include a change of momentum plate, a pivoted auger, a piezo-film based sensor, and a capacitive sensor. These prior art sensors are described briefly below.

Mass Flow Meters

A nuclear sensor (gamma ray) system consists of a gamma ray emitter, a detector, and a display unit. The material flows through a measuring gap between the emitter and detector. The number of photons registered by the detector is reduced by the material as it flows through the sensing volume. Material flow is calculated by the reduction of the number of photons. One problem with nuclear sensors relates to safety. Nuclear sensors use isotopes that require careful handling and extensive shielding. For example, for a nuclear sensor operating at 660 keV, shielding of approximately ½ inches of lead or 6–7 inches of steel may be required.

An impact-based sensor system may include strain-gage load cells, weigh pads (platform scales), and potentiometer load cells. All of these sensors use the same principle in determining the mass flow rate of agricultural product. These sensors measure the force exerted by the material as the material hits the sensing element, which is related to the flow rate of the material.

A change of momentum sensor includes a curved plate mounted at the exit of the clean gain elevator of a combine. Friction and impact forces change the direction of the material, such as an agricultural product, on the curved plate. The momentum of the agricultural product changes as the direction is forced to change on the flowing material. The difference in the average material speed is maintained constant between the inlet and outlet of the sensor. The mass flow rate is directly proportional to the force measured by a force transducer attached to the curved plate.

A capacitive sensor works on the principle that the dielectric constant of air/material mixture increases with increasing material concentration in a transport tube. The concentration of the material is determined by using capacitor plates around the transport tube. This method is claimed to be non-intrusive and insensitive to transmitted vibration. Calibration depends on the material being measured and varies with material distribution within the sensor.

With pivoted auger sensors, one end of an auger is supported by a load cell and the other end is pivoted. Agricultural product flows off the agricultural product auger into the pivoted end. The material is then carried by the pivoted auger and is discharged to a tank. The load cell mounted at the end of the pivoted auger measures the flow rate of the grain. The major drawback of this system is space limitations.

Belt conveyors are used primarily for potatoes, tomatoes, peanuts, sugar beets, and other agricultural products harvested with a conveyor belt. Load cells installed beneath the moving belt measure the amount of material being transported.

A piezo-film based impact sensor includes piezo-fum strips (high polar Poly-Vinylidene Film (PVDF)) which are mounted under sieves of combines. The impact of individual kernels are recorded as a measure of agricultural product flow rate. The sensor samples a portion of the material from the sieve.

Volumetric Flow Meters

A paddle wheel sensor consists of a number of paddle wheels. When agricultural product, for example, accumulates and reaches a certain height, the paddles are rotated by an electromagnetic clutch. The flow rate is determined by multiplying the number of revolutions per unit of time and the volume of the paddle wheel. The volumetric flow rate is converted to mass flow rate by using the density of the material being measured.

A photo-optical sensor is mounted near top of the clean grain elevator. The time interrupt of an infrared beam targeted at moving agricultural product is measured. This technique is used to estimate the volume of the flowing material.

An ultrasonic sensor is mounted above a collection bin. The ultrasonic sensor determines the depth or the change of depth of agricultural product in the bin. The change of depth is used to calculate the change of volume of agricultural product over a traveled distance.

In a Light Emitting Diode (LED) sensor, a strip of electronic sensors is mounted in the agricultural product bin. As the agricultural product level rises or falls, the sensor sends signals to LEDs which show the height of the agricultural product at certain levels. The volume of the agricultural product is then estimated. The LED measuring system could be equipped with 1, 4, 8, or 16 sensors.

The prior art flow sensors have been used to monitor the flow of agricultural materials such as grains (corn, soybeans, rice, wheat, etc.), high-value crops (potatoes, sugar beets, cotton, etc.), and straw coming out of combine harvesters and grain elevators as well as in feed and food processing plants. The accuracy of the combine flow sensors is claimed by manufacturers to be from 0.5 to 4% when installed and operated properly.

PROBLEMS IN THE ART

One problem with prior art flow rate sensors relates to the moisture content of biological materials. The dependence by most prior art devices on the moisture content readings introduces calibration for different types of agricultural products. Volume measuring systems require density of product to be known for a conversion into mass and variation of moisture has an impact on the accuracy of this conversion. Density variations may have an impact on the accuracy of momentum-based sensors as well due to the changes in the impact characteristics of materials with varying hardness.

Another problem with flow rate monitoring relates to noise caused by vibration if the monitoring is done on a moving implement or with respect to moving product. Noise impedes improvement in accuracy. When material flow is very small, the noise signal may become dominant. Below some threshold flow value, the flow rate is often assumed to be zero. This reduces the dynamic range of flow rates that can be determined by the agricultural product flow rate monitor.

Another problem with flow rate monitoring relates to the coating of agricultural product flow sensors. Coating problems may occur on certain types of prior art sensors which interact with the material (including soil and weeds, for example) during the agricultural product flow measurement. This reduces the sensitivity of the yield monitor.

Another problem with flow rate monitoring relates to some devices on mobile platforms such as combine harvesters. Depending upon the field slope the equipment is working on, flow characteristics of the crop changes and this has an impact on the accuracy of the measuring device.

Another important issue is the dependency of the yield sensors on frequent calibrations. Anything that changes the way the material flows through the transport system and anything that alters the way the material interacts with the sensing element would have an effect on the calibration accuracy of flow sensors. Thus, changes in material properties and flow dynamics would require recalibration of a yield sensor. Dependency on calibration makes flow rate sensors prone to errors.

Flow rate devices immune to the above problems would have large advantages over the devices requiring frequents calibrations to account for concerns summarized above.

FEATURES OF THE INVENTION

A general feature of the present invention is the provision of a method and apparatus for monitoring product or materials flow, including agricultural product flow, which overcomes problems found in the prior art.

A further feature of the present invention is the provision of a method and apparatus for monitoring product flow that uses x-ray techniques.

Further features, objects, and advantages of the present invention include:

a) A method and apparatus for monitoring product flow which uses x-ray techniques, which monitors the product flow while the product flows at various places such as combine harvesters, grain elevators, food processing plants, etc.

b) A method and apparatus for monitoring product flow which uses x-ray techniques, which does not impede the product flow.

c) A method and apparatus for monitoring product flow which uses x-ray techniques, which does not physically interact with the product itself.

d) A method and apparatus for monitoring product flow which uses x-ray techniques, which has a large dynamic range and a high sensitivity.

e) A method and apparatus for monitoring product flow which uses x-ray techniques, which is insensitive to product moisture content, particularly in agricultural products.

f) A method and apparatus for monitoring product flow which uses x-ray techniques, which is insensitive to product flow profile, as most products, including agricultural products do not fall or flow with the same amount of product across a cross section of the flow.

These as well as other features, objects, and advantages of the present invention will become apparent from the following specification and claims.

SUMMARY OF THE INVENTION

The flow rate measurement system of the present invention is an apparatus and method used to determine the flow rate of materials, including biological and agricultural products. The apparatus is comprised of an x-ray generator positioned near a flow of material such as agricultural product, a detector capturing the x-ray energy emitted by the generator and detecting intensity of x-ray radiation after passing through the flow of material, and a processor for processing the image to determine the material flow rate. The invention may optionally include a converter to convert detected x-ray radiation into visible light and/or an image intensifier coupled to or instead of the converter for enhancing intensity of light.

The method is comprised of directing x-ray energy through a flow of material, measuring the intensity of the x-ray energy after passing through the flow of material and correlating the intensity to flow rate of the material.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalencies which may be included within the spirit and scope of the invention.

In industry, x-ray attenuation is commonly used in material thickness gauging. The amount of material present in a sensing volume can be determined via x-ray attenuation measurements. The present invention uses x-ray techniques to determine the instantaneous flow rate of the materials, including agricultural products. In the preferred embodiment the flowing materials are agricultural products (grains, including corn and soybeans, vegetables, including potatoes, and beets, and others, e.g. cotton). For example, grain can be transferred through various means at mobile platforms such as combine harvesters, railway cars, trucks or at agricultural materials and food products processing and storage plants. In one embodiment the present invention can express the transmitted x-ray beam intensity in terms of gray scale values. These gray scale values can be correlated to the instantaneous agricultural product flow rate. Repeated measurements at a fast sampling rate (e.g. 30 Hz) and the integration of these readings over time (e.g. 1 sec.) allow the accurate monitoring of flow rate changes over time (described in detail below). X-ray tubes, similar to tubes used for dental x-rays, for example, do not present the safety issues at a scale that nuclear sensors do.

Figure 1:
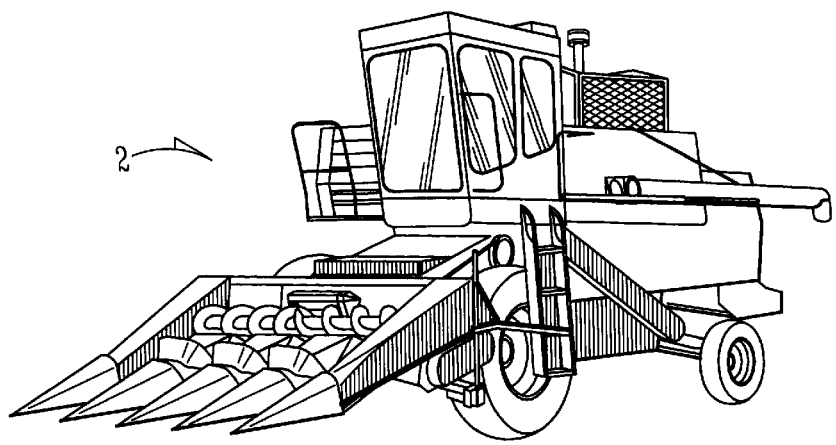
FIG. 1 is a perspective view of a conventional agricultural combine that can be used with the present invention.

FIG. 1 illustrates an agricultural combine 2, such as is known in the art. FIG. 1 depicts a combine (e.g. John Deere 4420 plot combine with 3-row corn head). The present invention can be used with such a machine as a yield monitor. Other applications are possible.

Figure 2:
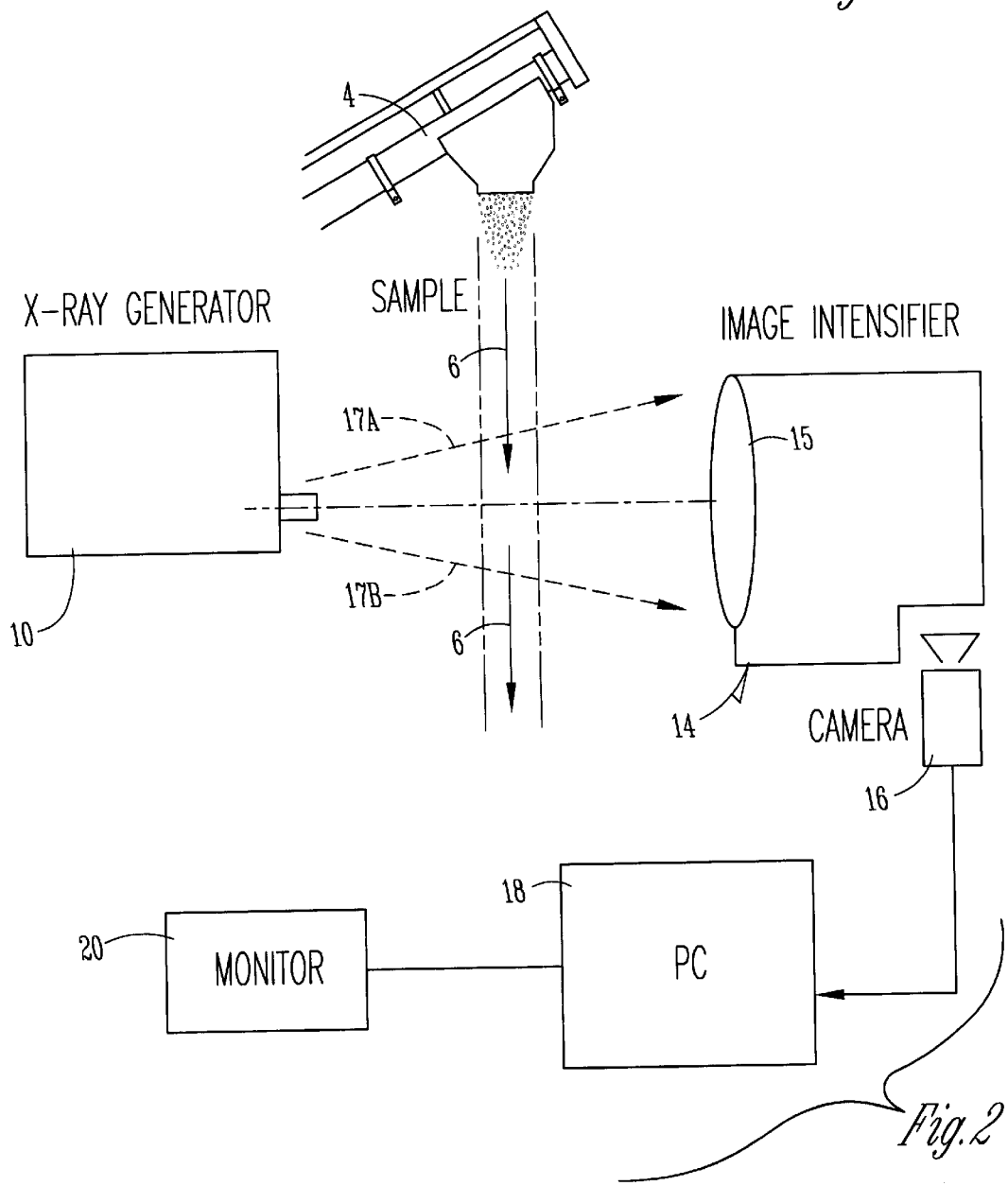
FIG. 2 is a block diagram of an embodiment of the present invention.

FIG. 2 is a block diagram of yield monitoring equipment to be installed on combine 2 for flow rate measurements. Monitor 20 shown in that block diagram is optional. An x-ray generator 10 is positioned near the flow of agricultural product 6 (e.g. corn) and transmits x-rays through the flow of agricultural product 6 in the direction shown. The agricultural product 6 is shown flowing out of an auger 4 of combine 2. It could be used with precision farming techniques and equipment. The yield monitoring equipment could be placed at other locations on combine 2, for example, in the path of harvested corn inside combine 2, or just before the harvested corn is dumped into the holding bin on combine 2.

The x-ray generator 10 is preferably comprised of an x-ray tube similar to an x-ray tube used for dental x-rays. An example is a Model FXT-200.50 x-ray generator from FienFocus Rontgen-Systems, 4405 International Blvd., Ste. C-103, Norcross, Ga. 30093. The x-ray generator 10 emits x-rays at a level of approximately 30–40 keV for products flowing in a free flow mode without any tubing surrounding the flowing material 6. For products flowing in a pipe or tube, this level is adjusted for specific application. An x-ray beam at these energy levels would require shielding of approximately ⅛ inches of lead. The x-rays that pass through the flow of agricultural product 6 strike a detector. Here the detector is medium 14 used for converting x-ray photons into visible light. The beam of x-rays is diagrammatically depicted by arrows 17A and 17B in FIG. 2. Depending upon the configuration, this medium may be a plate converting x-rays into visible light directly or it may be an image intensifier converting x-ray photons into visible light after enhancing intensity of light a couple of order of magnitudes. This works in a mode similar to night vision equipment. The block diagram in FIG. 2 shows the version with an image intensifier 14. The image intensifier 14 could include a lens 15 that focuses the visible light to a desired size. The visible image may be redirected by a mirror (not shown) or other type of device depending on what is desired before it is captured by the camera 16. The various ways to convert x-rays to visible light are well-known in the art.

Figure 3:
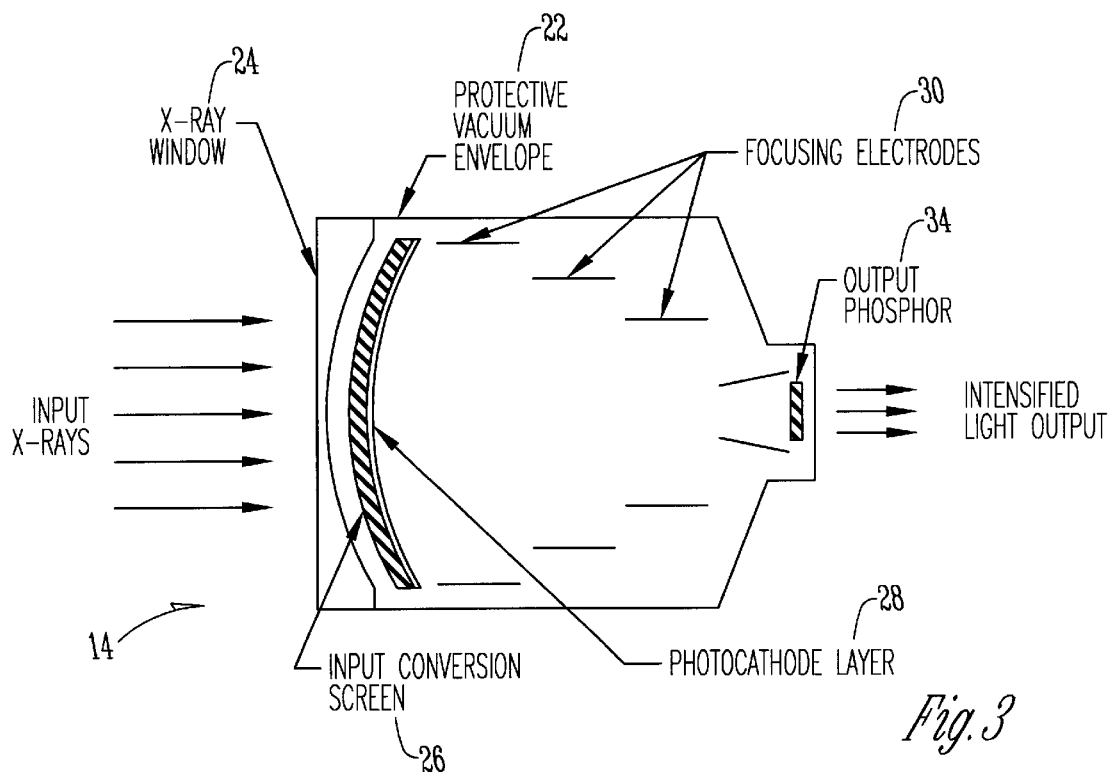
FIG. 3 is a diagrammatic depiction of a conventional image intensifier that can be used with the present invention.

FIG. 3 is a diagram of a conventional image intensifier such as could be used for medium 14 of FIG. 2. An example is a Model P593x image intensifier from Precise Optics/PME, Inc., 239 S. Fehr Way, Bay Shore, N.Y. 11706. Image intensifier 14 converts photons to electrons, accelerates the electrons, and then re-converts them to light. Image intensifiers typically operate in the range of 30 to 10,000 light amplification factors. The intensification is not necessarily solely electronic, but may also include a reduction in image area (electrons from a large area input screen are focused on a small area output screen).

As can be seen in FIG. 3, image intensifier 14 would be positioned to capture the x-rays from x-ray generator 10 after they have passed through the flowing stream of agricultural product 6. The x-rays would pass through a window 24 in the protective vacuum envelope 22 of image intensifier 14. Window 24 is at least substantially transparent to x-rays. The x-rays strike input conversion screen 26 (e.g. zinc-cadmium sulphide (ZnCds) or CsI(Na) or $Gd_2O_2S$), which converts the x-rays to light. A photocathode 28 adjacent to fluorescent layer or screen 26 converts the light to electrons. Focusing electrodes 30 accelerate and focus the electrons to phosphor output or viewing screen 34 by establishing a potential between photocathode 28 and viewing screen 34 (e.g. 25 kV–35 kV). Though not all of the light photons from screen 26 generate electrons at photocathode 28 and not all the accelerated electrons produce light at viewing screen 34, an increase in luminous flux is generated by the acceleration. Screen 26 is curved and has a larger diameter than screen 34. The reduction in diameter provides an additional factor of brightness gain.

A camera 16 is positioned near the image intensifier 14 and is aimed at the redirected visible image. In this way, the camera 16 captures the pattern and intensity of visible light emitted by the image intensifier 14 as a result of the x-rays which strike the plate 14. Camera 16 can be a CCD camera, such as are well known in the art, for example a Model 4900 Series High Performance Monochrome CCD Camera from COHU, Inc. of 5755 Kearny Villa Rd., San Diego, Calif. 92123. A frame grabber (e.g. 30 frames/sec.) and processor (e.g. Model DT2867, Data Translation, Inc., 100 Lock Drive, Marlboro, Mass. 01752-1192) could be used with camera 16. The camera 16 is connected to a personal computer (PC) 18 (e.g. IBM compatible PC) which in turn is connected to a conventional video monitor (e.g. Sony Trinitron Monitor). The monitor 20 may show the visible pattern and intensity of light emitted by the image intensifier 14. The PC 18 is used to analyze the data captured by the camera 16 (described in detail below).

A charge-coupled-device (CCD) is a solid-state device comprised of closely spaced single- or multiple-capacitor imaging elements, called pixels. Linear or area configurations of the pixels, with the appropriate on-chip scanning circuit and low-noise preamplifier, constitute the focal-plane image sensor in a camera system. Most CCD cameras have on the order of a 500×300 pixel format. Each pixel is essentially a photo-sensitive device which generates an accumulated charge proportional to the incident light flux it experiences. An image is thus possible by transferring the entire charge pattern for a given time to a storage device. It can be digitized and thus available for processing by a digital computer on a pixel-by-pixel basis. Pixels with higher charges are processed to produce a video signal of a higher gray scale. Pixels with lower charges are processed to produce a video signal of a lower gray scale. Thus, the CCD output not only indicates points in the pixel area that received light, but also how much light by the gray scale associated with each pixel.

Figure 4:
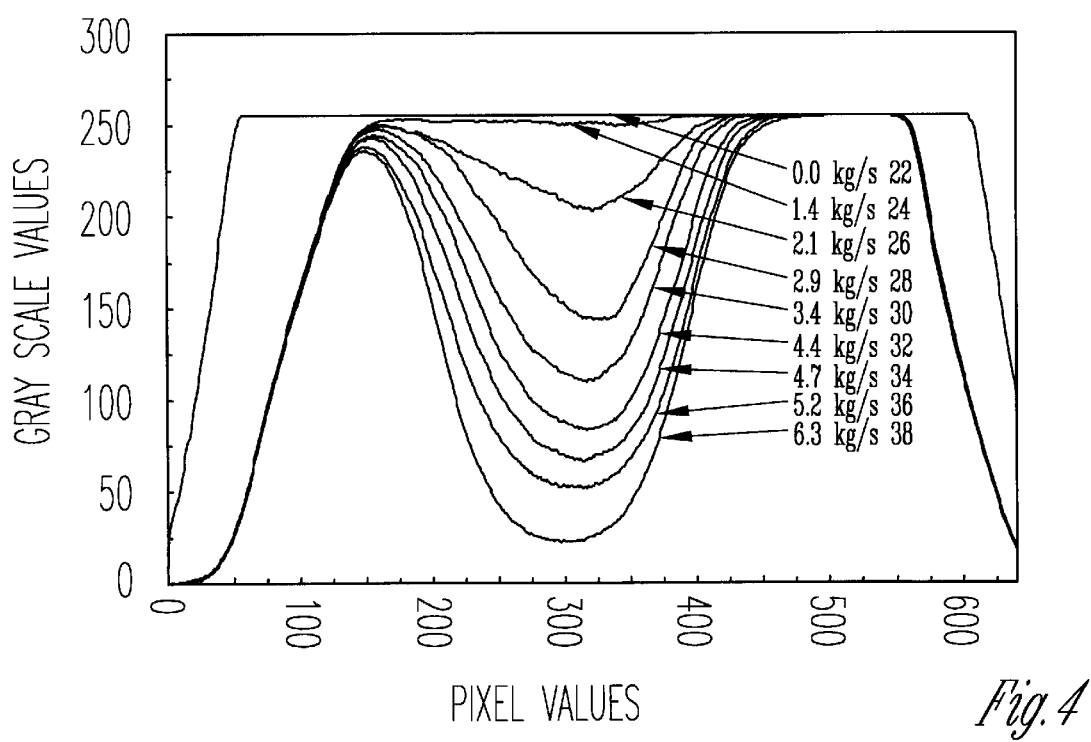
FIG. 4 is a diagram showing profiles of agricultural product for various flow rates.

The PC 18 accepts the gray scale values forming the captured image from the camera 16 and uses these values to determine flow rate. By monitoring the gray scale values, an indication of the agricultural product flow rate can be determined. In order to obtain an accurate result, a number of successive measurements (30/sec.) are taken and analyzed. FIG. 4 is a plot of average gray scale values at various flow rates (0.0 kg/s to 6.3 kg/s) versus the pixel value on the monitor 20. The term "pixel value" refers to the pixel position in a row of pixels on monitor 20. In this embodiment, there are 480 rows of pixels with 640 columns of pixels. Therefore, there are 640 pixels in each row. Pixel value 1 is the first pixel on one side of a row on monitor 20 and pixel value 640 is the last pixel on that row (i.e. on the other side of the monitor screen). Thus FIG. 4 is illustrating the gray scale values across one row or line of monitor 20 for the various flow rates (here corn but other materials are possible), and relates to the amount of x-ray energy that made it through a slice of the flowing agricultural product. Since a flow of agricultural product in a free fall mode is typically thicker in the center, and thinner at the sides, the U-shaped lines shown in FIG. 4 result. Note that only the data between approximately pixel 150 and 450 is relevant, since the gray scale values outside this range do not represent the image affected by the flowing agricultural product. FIG. 4 illustrates average gray scale values for the flow rates indicated for each curve in FIG. 4, with the flow rate of 0.0 indicating no flow whatsoever.

Figure 5:
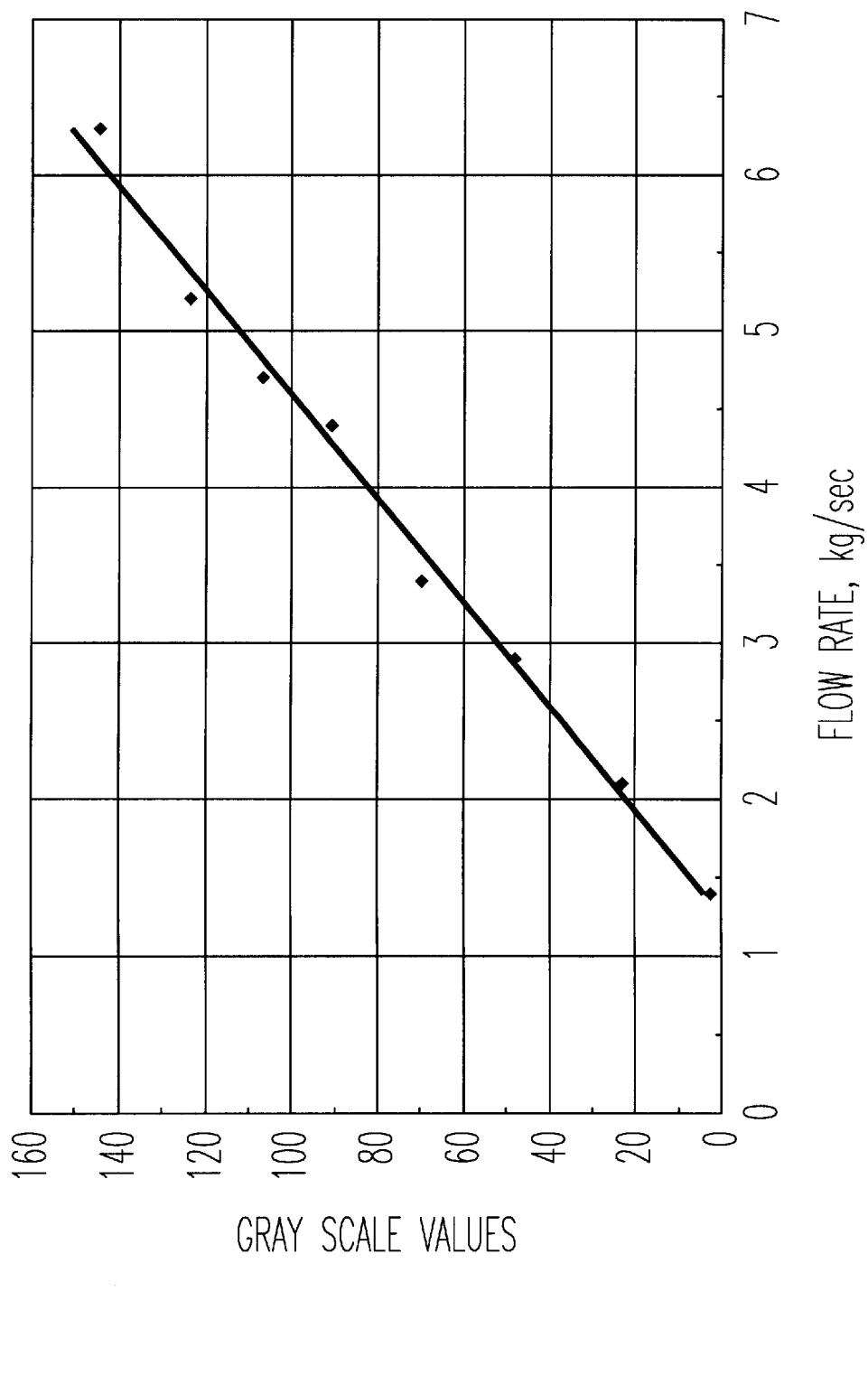
FIG. 5 is a diagram showing the gray scale difference versus the flow rate for the present invention.

As shown, as the flow rate increases, the gray scale value decreases. The gray scale values for each flow rate were integrated for pixel values between 150–450 (covering the width of the flowing agricultural product). Sums were divided by the number of pixel values (300) and then were subtracted from 255. The resulting value was taken as the representative gray scale difference value at the corresponding flow rate. These gray scale values are plotted against the flow rates in FIG. 5. FIG. 5 therefore illustrates the relationship between agricultural product flow rate and the gray scale values. The invention is capable of achieving accuracy levels of 1% without exhaustive data processing.

Thus, by a priori testing with known flow rates, the curves of FIG. 4 can be developed. As described above, by integration, division by 300 and subtraction from 255 ($2^8-1$ gray scale values), the gray scale difference value for each curve is established. These gray scale difference values, the data points illustrated at FIG. 5, uniquely characterize their respective curves of FIG. 4, which are based on the gray scale values determined for each flow rate. As shown in FIG. 5, the gray scale difference values line up well along the linear fit line. Therefore, measurements of gray scale values across a row of a CCD camera can be input into processor 18 and processed into a flow rate.

Figure 6:
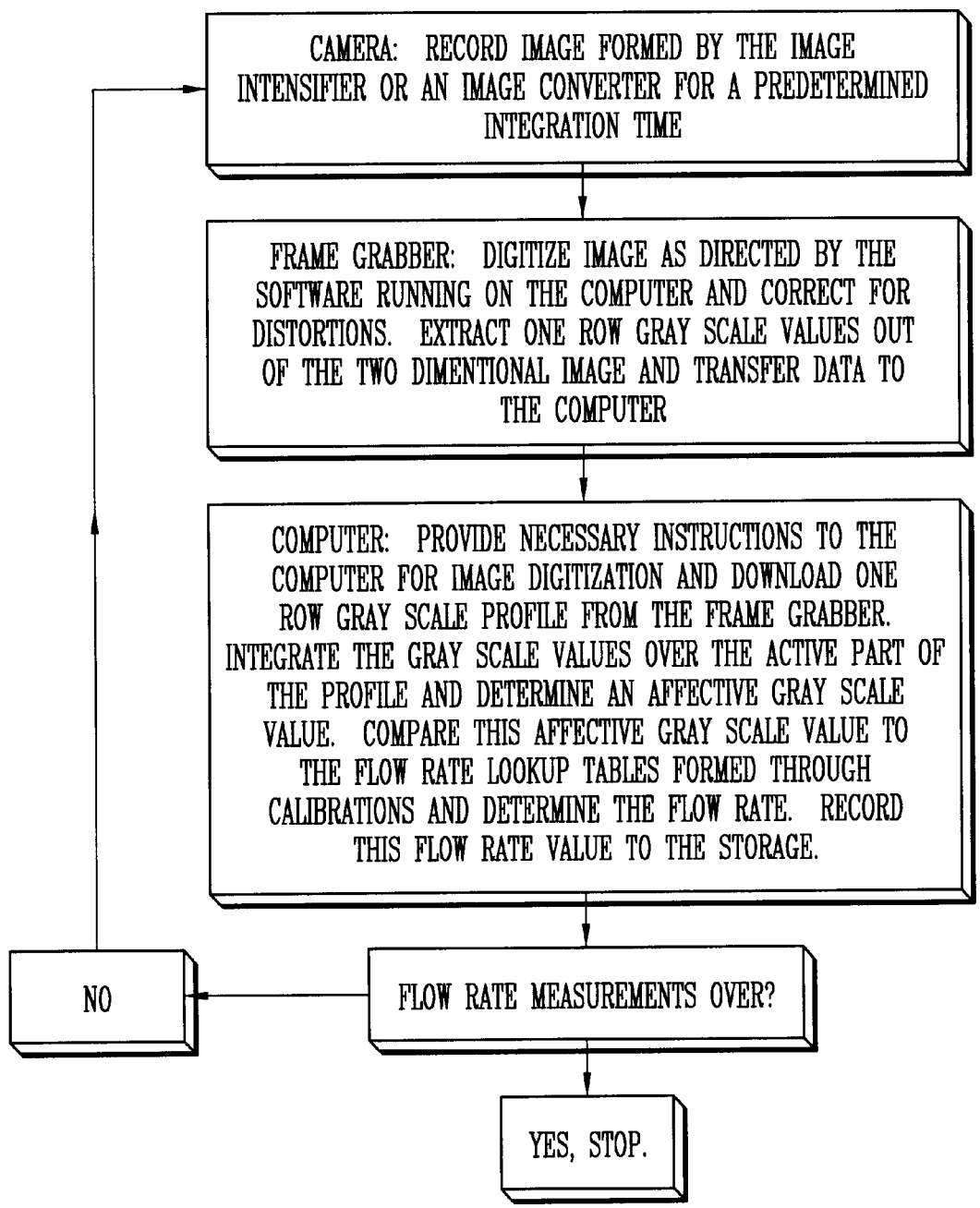
FIG. 6 is a flow diagram of software according to an embodiment of the invention.

FIG. 6 is a flow chart of operation of the combination of FIG. 2. The flow chart assumes that x-ray generator 16 is on and product 6 is flowing.

In order to improve the performance of the camera 16, the data captured by the camera 16 is processed by the PC 18 with software which follows the mathematical steps outlined above. Preferably, in order to get rid of noise in the signal, a number of samples may be added up to obtain a better signal to noise ratio. Alternately, the samples could be averaged.

As mentioned above, prior art devices must be calibrated to compensate for the moisture content of agricultural product. However, the moisture content of agricultural product does not affect the measurements significantly done using x-ray techniques. Therefore, the present invention does not have to be calibrated to compensate for moisture content.

In an alternate embodiment of the present invention, the image intensifier 14 is not used. In this alternate embodiment, the camera 16 is used in conjunction with a plate 14, which could be the type of plate used in night vision equipment. The data obtained is processed in order to get a high enough resolution to be useful. In addition, the invention could be used to determine flow rates of other particulate or even liquid materials.

The preferred embodiment of the present invention has been set forth in the drawings and specification, and although specific terms are employed, these are used in generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

For example, the flowing material may be a variety of materials in a variety of states. It could be biological product, including agricultural products. Grain is but one example. Vegetables (e.g. beets) is another example. Cotton is a still further example.

The manner in which the x-ray energy is detected after passing through the flowing material can vary. In the preferred embodiment, the x-ray energy is detected and converted to visible light. Examples have been discussed above. Others are possible. The intensity of the visible light is captured for processing. A CCD camera is discussed. Other ways are possible. Other solid state cameras might be used.

Although the described technique involves an image intensifier coupled with a CCD camera together forming a detector to measure the intensity of the x-rays passing through the flowing biological material, this is not the only detector type that can be used in measurements. There is a large variety of detectors that can be configured into an array structure for substituting image intensifier camera pairs described here. The various scintillation detectors can easily be forged into array detectors. Newly emerging amorphous silicon detectors can also easily be used in the measuring technique described here.

What is claimed is:

1. A flow rate monitor for material comprising an agricultural product comprising:
   an x-ray generator positionable near a flow path of material, the x-ray generator being oriented to transmit x-rays through a flow of material along said flow path;
   a detector positionable near the flow path of material generally opposite the x-ray generator to receive x-rays after passage through material flowing along said flow path and derive intensity of received x-rays.

2. The flow rate monitor of claim 1 wherein the material is a flowing material.

3. The flow rate monitor of claim 1 wherein the agricultural product is a grain.

4. The flow rate monitor of claim 1 wherein the detector has an array structure.

5. The flow rate monitor of claim 1 wherein the detector comprises a converter for converting x-ray radiation into visible light, the converter being positioned near the flow of material such that the x-rays emitted through the material flow strike the converter; an image capture device operatively positioned relative to the converter to capture images of the visible light emitted by the converter; a processor for processing the images to determine the material flow rate.

6. The flow rate monitor of claim 5 wherein the image capture device is a camera.

7. The flow rate monitor of claim 6 wherein the camera is a solid state imager.

8. The flow rate monitor of claim 7 wherein the solid state imager is a charge coupled device.

9. The flow rate monitor of claim 5 wherein the converter comprises an image intensifier converting x-rays and intensifying the visible light before the image capture device captures images of the visible light.

10. The flow rate monitor of claim 5 wherein the processor processes the images by correlating the intensity of visible light captured in the images to a flow rate.

11. The flow rate monitor of claim 5 wherein the processor processes images relayed by the image capture device by summing the grayscale values of the multiple images and integrating the summed grayscale values.

12. The flow rate monitor of claim 5 wherein the processor includes a memory and software on the memory, the software including instructions to process the captured images.

13. A flow rate monitor comprising:
   an x-ray generator positioned near a flow of material, the x-ray generator being oriented to transmit x-rays through the flow of material;
   a detector positioned near the flow of material to receive the x-rays after passage through the material and derive intensity of the received x-rays;
   the material comprising a flowing biological material, the biological material comprising an agricultural product, the agricultural product comprising a grain.

14. A flow rate monitor comprising:
   an x-ray generator positioned near a flow of material, the x-ray generator being oriented to transmit x-rays through the flow of material;
   a detector positioned near the flow of material to receive the x-rays after passage through the material and derive intensity of the received x-rays;
   the detector comprising a converter for converting x-ray radiation into visible light, the converter being positioned near the flow of material such that the x-rays emitted through the material flow strike the converter; an image capture device operatively positioned relative to the converter to capture images of the visible light emitted by the converter; a processor for processing the images to determine the material flow rate, the processor processes images relayed by the image capture device by summing grayscale values of portions of the multiple images and then integrating the summed grayscale values.

15. The flow rate monitor of claim 2 wherein the flowing material is a biological material.

16. An apparatus for determining flow rate of a flowing material comprising agricultural product comprising:
   a device to create a flow of material;
   an x-ray generator adapted to transmit x-ray radiation toward the flow of material;
   an x-ray detector adapted to detect x-ray radiation which is transmitted through the flow of material and convert the detected x-ray radiation into pixel data; and
   a processor for processing the pixel data to determine the material flow rate.

17. The apparatus of claim 16 wherein the x-ray detector converts multiple samples of the detected radiation into multiple samples of pixel data.

18. The apparatus of claim 17 wherein the processor processes the multiple samples of pixel data to determine the material.

19. The apparatus of claim 17 wherein the processor processes the multiple samples of pixel data by combining the multiple samples of pixel data, correlating the combined pixel data to a flow rate value.

20. The apparatus of claim 19 wherein the processor combines the multiple samples of pixel data by:

converting each sample of pixel data to a value;

summing the values of the multiple samples; and integrating the summed values.

21. The flow rate monitor of claim 16 wherein the material is a biological material.

22. A method of measuring the flow rate of material comprising the steps of:

providing a flow of material;

transmitting x-ray radiation through the flow of material;

detecting the x-ray radiation after passing through the flow of material comprising converting the detected x-ray radiation into visible light; converting the visible light to a gray scale image;

correlating intensity of the detected x-ray radiation to flow rate of the material;

the material comprising a biological material comprising an agricultural product comprising grain.

23. A method of measuring the flow rate of material comprising agricultural product comprising the steps of:

providing a flow of material;

transmitting x-ray radiation through the flow of material;

detecting the x-ray radiation after passing through the flow of material;

correlating intensity of the detected x-ray radiation to flow rate of the material.

24. The method of claim 23 wherein the detecting step further comprises converting the detected x-ray radiation into visible light; converting the visible light to a gray scale image; and determining the material flow rate based on the gray scale image.

25. The method of claim 24 further comprising the step of intensifying the visible light before the light is converted into a gray scale image.

26. The method of claim 24 further comprising the step of converting multiple samples of the visible light into multiple gray scale images.

27. The method of claim 26 further comprising the step of summing the multiple grayscale images together.

28. The method of claim 27 further comprising the step of integrating the summed multiple grayscale images.

29. The method of claim 28 further comprising the step of correlating the integrated images to a flow rate.

30. The method of claim 23 wherein the agricultural product is grain.

31. The method of claim 24 further comprising creating a prior database of gray scale values correlated to flow rates, and comparing the gray scale image to the prior database.

32. The flow rate monitor of claim 23 wherein the material is a biological material.

33. An apparatus for determining flow rate of a flowing material comprising:

a device to create a flow of material;

an x-ray generator coupled to the device to transmit x-ray radiation toward the flow of material;

an x-ray detector coupled to the device to detect the x-ray radiation which is transmitted through the flow of material and convert the detected x-ray radiation into pixel data; and a processor for processing the pixel data to determine the material flow rate;

the x-ray detector converts multiple samples of the detected radiation into multiple samples of pixel data;

the processor processes the multiple samples of pixel data by combining the multiple samples of pixel data, correlating the combined pixel data to a flow rate value by:

summing pixel data of the multiple samples;

integrating the summed pixel data.

34. A method of measuring the flow rate of material comprising the steps of:

providing a flow of material;

transmitting x-ray radiation through the flow of material;

detecting the x-ray radiation after passing through the flow of material comprising converting the detected x-ray radiation into visible light; converting the visible light to a gray scale image;

correlating intensity of the detected x-ray radiation to flow rate of the material based on the gray scale image;

further comprising the step of converting multiple samples of the visible light into multiple gray scale images and summing the multiple grayscale images together.

35. The method of claim 34 further comprising the step of integrating the summed multiple grayscale images.

36. The method of claim 34 further comprising the step of correlating the integrated images to a flow rate.

* * * * *

UNITED STATES PATENT AND TRADEMARK OFFICE
CERTIFICATE OF CORRECTION

PATENT NO.    : 6,526,120 B1
DATED         : February 25, 2003
INVENTOR(S)   : Joseph N. Gray, Feyzi Inanc and Selcuk Arslan It is certified that error appears in the above-identified patent and that said Letters Patent is hereby corrected as shown below:

<u>Column 1,</u>
Line 8, insert:
-- GRANT REFERENCE

Work for this invention was funded in part by a grant from the United States Department of Energy, Contract No. W-7405-Eng-82. The government may have certain rights in this invention. --

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,526,120 B1
DATED : February 25, 2003
INVENTOR(S) : Joseph N. Gray, Feyzi Inanc and Selcuk Arslan It is certified that error appears in the above-identified patent and that said Letters Patent is hereby corrected as shown below:

Title page,
Item [73], Assignee, should read -- Iowa State University Research Foundation, Inc. Ames, Iowa 50011-2131 --.

Signed and Sealed this

Thirty-first Day of January, 2006

JON W. DUDAS
*Director of the United States Patent and Trademark Office*